US005249583A

United States Patent [19]

Mallaby

[11] Patent Number: 5,249,583
[45] Date of Patent: Oct. 5, 1993

[54] ELECTRONIC BIOPSY INSTRUMENT WITH WIPERLESS POSITION SENSORS

[75] Inventor: Mark Mallaby, Bloomington, Ind.

[73] Assignee: Vance Products Incorporated, Spencer, Ind.

[21] Appl. No.: 973,533

[22] Filed: Nov. 9, 1992

Related U.S. Application Data

[63] Continuation of Ser. No. 649,447, Feb. 1, 1991, abandoned.

[51] Int. Cl.$^5$ ............................................. A61B 10/00
[52] U.S. Cl. ................................... 128/754; 128/755; 606/171
[58] Field of Search ............... 128/749, 751, 754, 755, 128/752, 753; 606/167, 170, 171

[56] References Cited

U.S. PATENT DOCUMENTS

| 3,561,429 | 2/1971 | Jewett . | |
|---|---|---|---|
| 4,020,555 | 5/1977 | Hedrick | 30/392 |
| 4,243,048 | 1/1981 | Griffin . | |
| 4,461,305 | 7/1984 | Cibley . | |
| 4,589,414 | 5/1986 | Yoshida et al. . | |
| 4,600,014 | 7/1986 | Beraha . | |
| 4,605,011 | 8/1986 | Näslund . | |
| 4,651,752 | 3/1987 | Fuerst . | |
| 4,667,684 | 5/1987 | Leigh . | |
| 4,699,154 | 10/1987 | Lindgren . | |
| 4,702,260 | 10/1987 | Wang . | |
| 4,732,096 | 3/1988 | Mall | 112/121.12 |
| 4,940,061 | 7/1990 | Terwilliger et al. . | |
| 4,974,535 | 12/1990 | Plassmeier et al. | 112/262.1 |
| 4,982,739 | 1/1991 | Hemstreet et al. . | |
| 4,989,614 | 2/1991 | Dejter, Jr. et al. | 128/752 |
| 5,048,538 | 9/1991 | Terwilliger et al. | 128/754 |
| 5,050,405 | 9/1991 | Jacobsson | 66/132 R |
| 5,146,921 | 9/1992 | Terwilliger et al. | 128/754 |
| 5,171,255 | 12/1992 | Rydell | 606/170 |

FOREIGN PATENT DOCUMENTS 494028 6/1950 Belgium .
0198926 10/1986 European Pat. Off. .
0365377 4/1990 European Pat. Off. .

OTHER PUBLICATIONS

Roberts, S., "Reliable Sensing with Optoelectronics," Machine Design 50:1, pp. 104–109 (1978).

Primary Examiner—Max Hindenburg
Assistant Examiner—Guy V. Tucker
Attorney, Agent, or Firm—Woodard, Emhardt, Naughton Moriarty & McNett

[57] ABSTRACT

An instrument for removing tissue samples from a tissue mass which automatically penetrates, severs, and removes a tissue portion for examination. The instrument is motor powered, preferably by self-contained rechargeable batteries, and employs electrically actuated stops to control the action of penetration into and retraction from the tissue mass. The tissue penetrating means and severing means includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a motor powered rotary cam assembly by means of cam followers and the rotary motion of the cam is converted to sequential, linear motion in the tissue penetrating means and severing means. The angular position of a cam is monitored with a pair of optoelectronic sensors, thereby providing position feedback without mechanical wear on the position sensor assembly. Improved action is provided by a cam having an S-curve profile.

14 Claims, 6 Drawing Sheets

ELECTRONIC BIOPSY INSTRUMENT WITH WIPERLESS POSITION SENSORS

This application is a continuation of application Ser. No. 07/649,447, filed Feb. 1, 1991, now abandoned.

FIELD OF THE INVENTION

This invention relates to an instrument for extracting samples of tissue from humans and other animals and more particularly to an instrument for automatically performing a biopsy of a tissue mass in an accurate, expeditious manner with a minimum of discomfort to the patient.

BACKGROUND OF THE INVENTION

It is often desirable and frequently absolutely necessary to sample or test a portion of tissue from humans and even other animals, particularly in the diagnosis and treatment of patients with cancerous tumors, pre-malignant conditions and other diseases or disorders. Typically in the case of cancer, when the physician establishes by means of procedures such as palpitation, x-ray or ultra sound imaging that suspicious circumstances exist, a very important process is to establish whether the cells are cancerous by doing a biopsy. Biopsy may be done by an open or closed technique. Open biopsy removes the entire mass (excision biopsy) or a part of the mass (incision biopsy). Closed biopsy on the other hand is usually done with a needle-like instrument and may be either an aspiration or a core biopsy. In needle aspiration biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy depends in large part in circumstances present with respect to the patient and no single procedure is ideal for all cases. However, core biopsy is extremely useful in a number of conditions and is being used more frequently by the medical profession.

A variety of biopsy needles and devices have been described and used for obtaining specimens of tissue. For example, reference is made to U.S. Pat. Nos. 4,651,752; 4,702,260; and 4,243,048 which show biopsy needles of varying types. Additionally, a number of very specialized devices for extracting samples of tissue have been described such as the biopsy device in U.S. Pat. No. 4,461,305, which device is designed specifically for removing a sample of tissue from the female uterine cervix. Other devices have been disclosed which relate to surgical cutting instruments. For example, U.S. Pat. No. 4,589,414 discloses an instrument which is particularly designed to operate in the area of the knee to withdraw tissue chips. Also available are so-called biopsy guns for removing a core of tissue which customarily are spring powered devices and must be cocked with considerable force. When actuated such guns produce a loud snapping noise, combined with a jerking action. Such a biopsy gun may employ a needle set consisting of an inner stylet and an outer tube called a cannula. The stylet is a needle like device with a notched cut-out at its distal end. The cannula in effect is a hollow needle with an angled cutting surface at its distal end which slides over the stylet. When the stylet is forced into tissue, the tissue is pierced and relaxes into the notched cut-out of the stylet. When the cannula is then slid forward, the tissue in the notch of the stylet is sliced off and retained in the notch until the cannula is withdrawn. Examples of such devices are shown in U.S. Pat. Nos. 4,600,014 and 4,699,154. Although such spring powered biopsy guns will remove a core or sample of tissue, they have rather serious disadvantages. For one, they must be manually cocked with a plunger bar. Such "cocking" of the gun requires considerable force and the gun must be cocked for each biopsy cut. A further disadvantage is that the springs provided in the gun accelerate the needles until a mechanical stop position is reached, creating a loud snapping noise and jerking motion which is a problem both to the physician and the patient. This noise and jerking action can cause the patient to jump and in some cases even prevents the physician from striking the intended tissue target. Another disadvantage is that the force and velocity delivered to the stylet and cannula rapidly diminishes when traveling from a retracted to a fully extended position resulting in tissue samples of lower quality.

U.S. Pat. No. 4,940,061 discloses a biopsy instrument which represents a substantial improvement over the aforementioned devices, substantially eliminating the loud snapping noise and jerking motion associated with spring-powered biopsy guns, for example. In the instrument of Pat. No. 4,940,061, an electric motor drives a rotary cam assembly which converts rotary motion to linear motion to sequentially extend and retract a stylet and cannula, and employs electrically actuated stops to control the extension and retraction of the stylet and cannula. Details of the construction and operation of the biopsy instrument are disclosed in U.S. Pat. No. 4,940,061, which is hereby incorporated by reference. Although well suited for many applications, that instrument suffers certain drawbacks, one of them being mechanical wear associated with a limit switch assembly and a toggle assembly which both include stationary wiper plates and spring finger contacts which slide against each other during normal operation.

Accordingly it is a principal object of this invention to provide an instrument for obtaining samples of tissue from tissue masses.

It is another object of this invention to provide an instrument for automatically performing a biopsy of a tissue mass in an accurate and expeditious manner with a maximum of accuracy and a minimum amount of discomfort to the patient.

It is a still further object of this invention to provide an instrument for performing tissue mass biopsies by removing a core or sample of tissue, which instrument eliminates the need for springs and mechanical stops, which is silent in operation and has the ability to effectively penetrate even small tissue masses.

It is another object of this invention to provide an instrument for obtaining tissue samples from tissue masses which instrument requires no manual setting or cocking and which may be "fired" multiple times without any abrupt starts or stops.

It is still another object of this invention to provide a biopsy instrument which includes means to convert rotary motion to sequential, linear motion of substantially constant force and velocity to the means for penetrating and severing a tissue sample from a tissue mass.

These and other objects of the invention will be apparent from the following description and claims.

SUMMARY OF THE INVENTION

Based on the prior art instruments for biopsy samples from tissue masses, and the actual present state of this art, there then exists a need for an instrument which is capable of automatically removing a tissue sample or core sample of predetermined size where the process is done very rapidly, is easily repeated if required, is accurate, is relatively simple for the physician to use, is virtually noiseless, and in use results in minimal discomfort to the patient.

Accordingly, I have invented an instrument for removing tissue samples from a tissue mass which instrument automatically penetrates, severs, and removes the tissue portion for examination. The instrument is motor powered, preferably by self-contained rechargeable batteries, and employs electrically actuated stops instead of mechanical stops to control the action of penetration and retraction from the tissue mass. The portion of the instrument which penetrates the tissue mass and severs a portion thereof, the tissue penetrating and severing means, includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a special motor powered rotary cam assembly by means of cam followers and it is a feature of this invention that the rotary motion of the cam is converted to sequential, linear motion in the tissue penetrating and severing means, the linear motion being of substantially constant force and velocity.

In operation, the physician or technician actuates the instrument by pressing a button causing the stylet to move forward in a rapid, precise manner and penetrate the tissue mass followed with penetration of the mass by the cannula, resulting in a portion or core of tissue being severed and retained in the notched portion of the stylet. Further actuation by the physician causes the cannula to retract exposing the tissue sample in the stylet for easy removal. An additional actuation causes retraction of the stylet and a resetting of the cannula/stylet assembly for further use.

BRIEF DESCRIPTION OF THE DRAWINGS

The above noted advantages and other characteristic features of the present invention will be in part apparent from the accompanying drawings, and in part pointed out in the following detailed description of the preferred embodiment of the invention in which reference will be made to the accompanying drawings wherein like reference numerals designate corresponding parts and wherein.

DESCRIPTION OF THE PREFERRED EMBODIMENT

Figure 1:
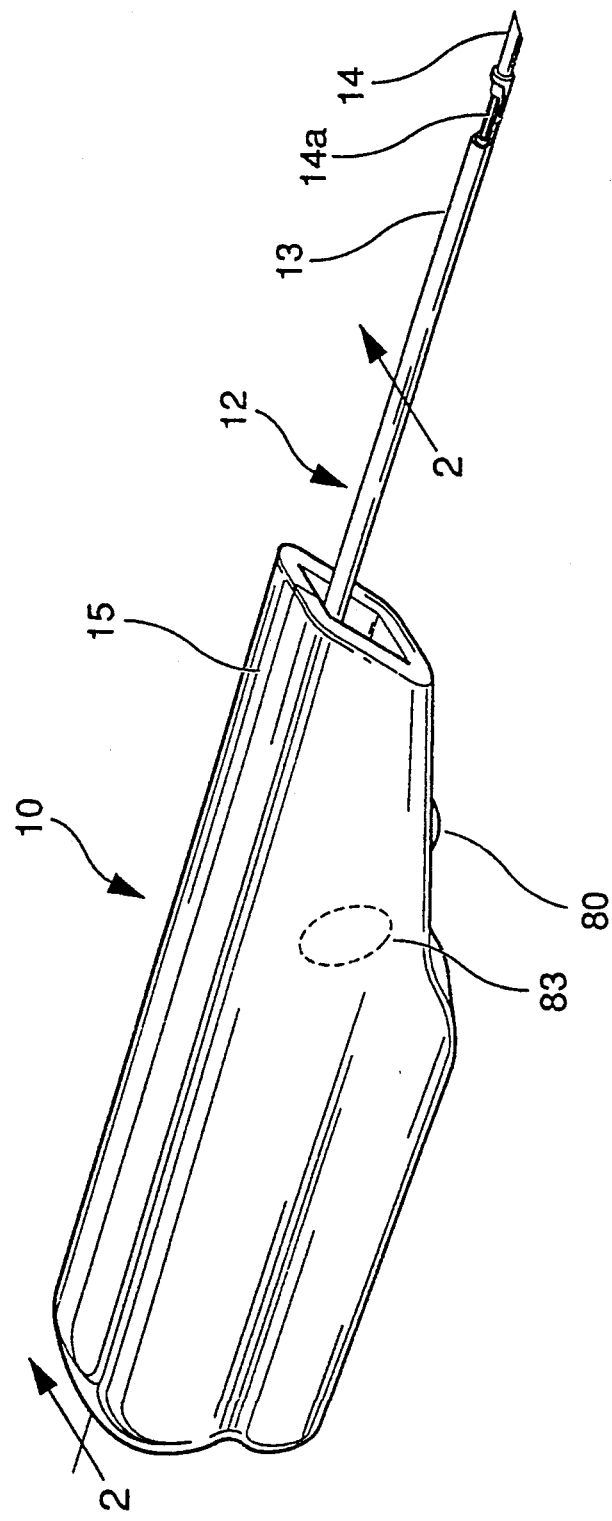
FIG. 1 is a perspective view of the biopsy instrument of this invention.

For the purposes of promoting an understanding of the principles of the invention, reference will now be made to the embodiment illustrated in the drawings and specific language will be used to described the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
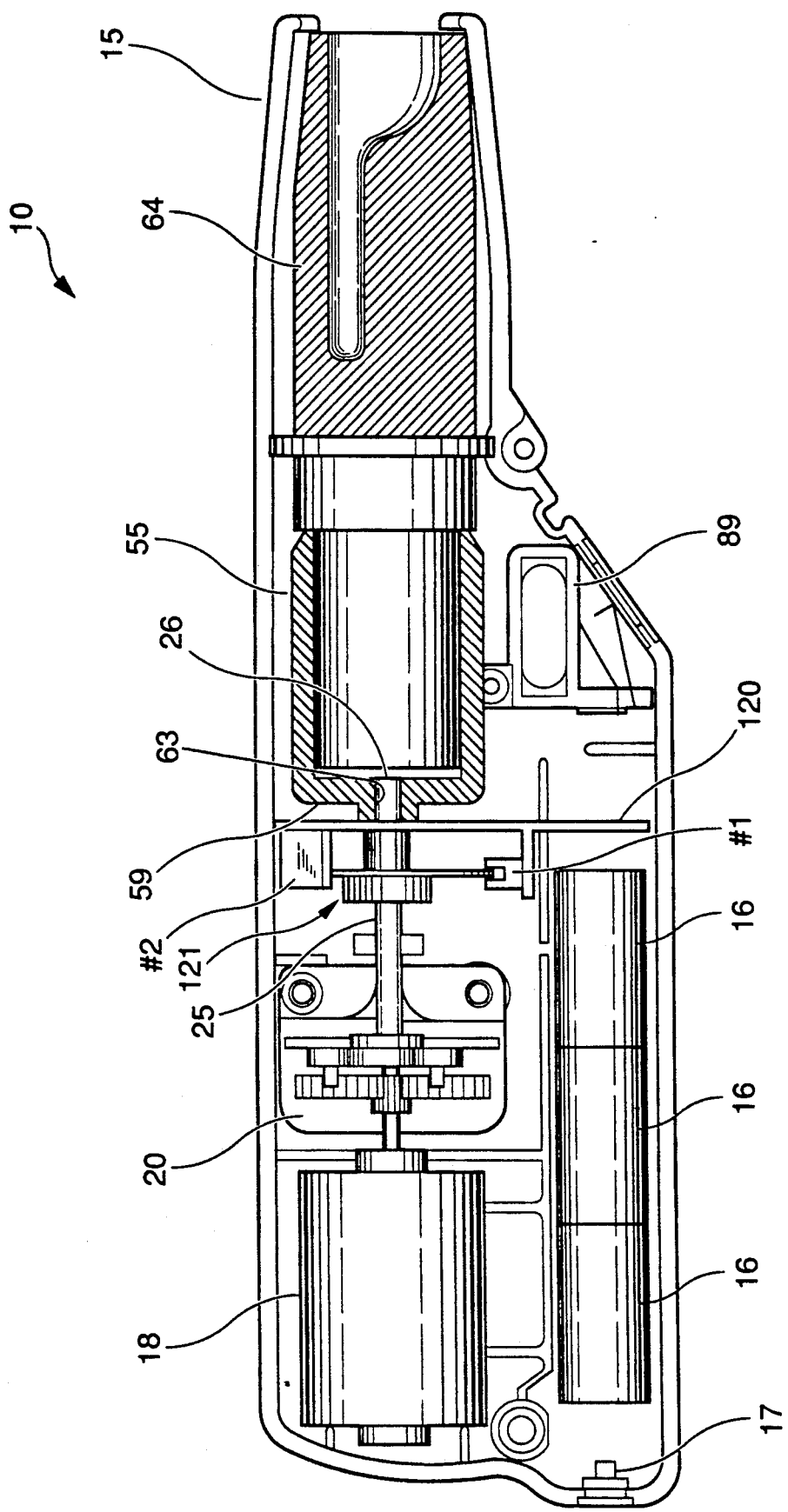
FIG. 2 is a side elevational view taken on the line 2—2 of FIG. 1.
Figure 3:
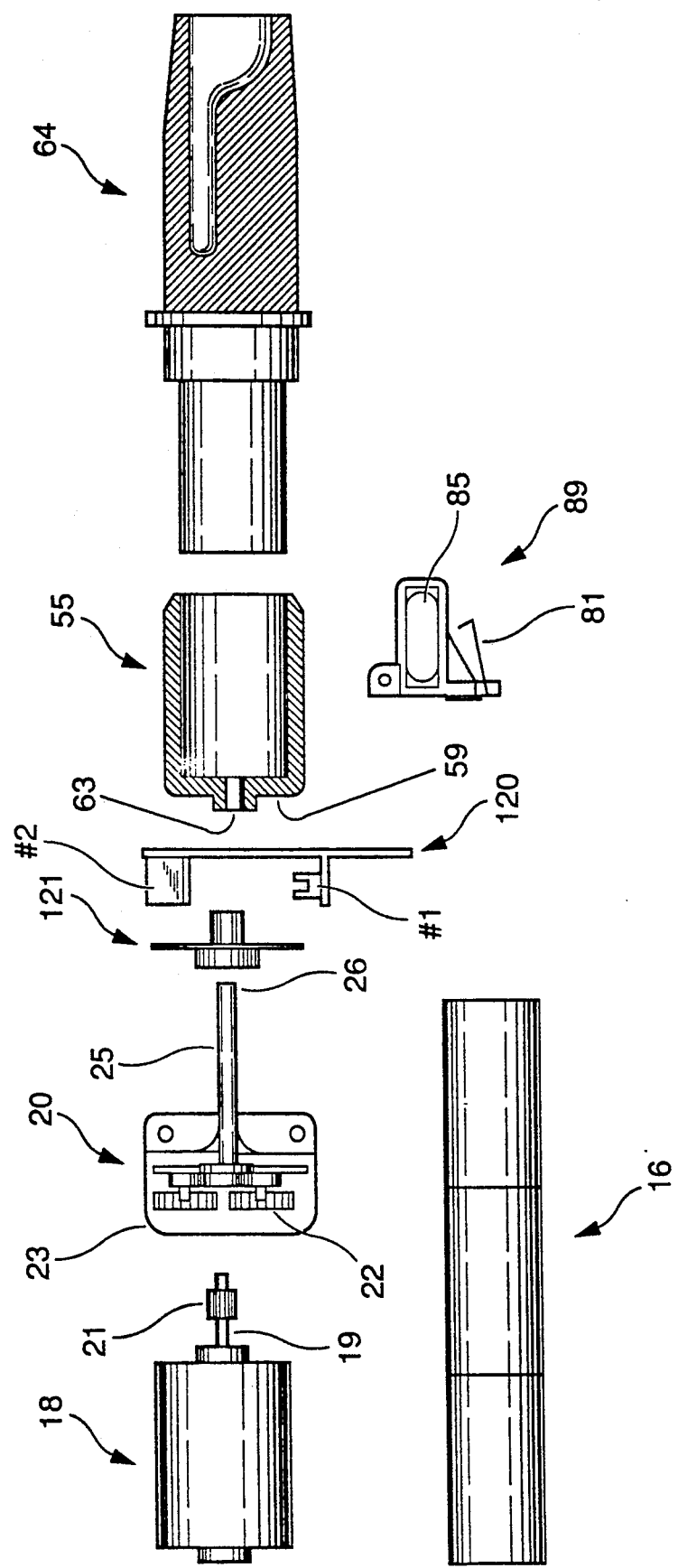
FIG. 3 is an exploded view of the major component parts of the instrument shown in FIG. 2.

Considering now the drawings in detail, FIG. 1 illustrates a perspective view of one embodiment of the inventive biopsy instrument which is shown generally at 10 with the tissue piercing and removing means shown generally at 12. The tissue piercing and removing means comprises a stylet 14 and cannula 13. Referring to FIG. 2 which is a sectional view through the instrument shown in FIG. 1, and FIGS. 3 and 4, which are exploded views of a number of the components of the instrument, the instrument 10 is shown as having an outer housing 15 provided with a motor 18 mounted in one end thereof. Motor 18 is reversible and preferably of the DC type and preferably powered by rechargeable batteries 16 contained within the housing. Suitable contacts 17 are provided to recharge the batteries. Motor 18 is operably engaged with planetary gear assembly 20 by means of shaft 19 which shaft engages central gear 21. Central gear 21 in turn meshes with planetary gears 22 which in turn engage with annulus gear 23. In a preferred embodiment the DC motor operates at about 10,000 rpm with the gearing being about a 6:1 ratio. Drive shaft 25 is secured at its end 26 in the D-shaped opening 35 of the planetary gear set by means of a set screw or other suitable fastening means.

Figure 4:
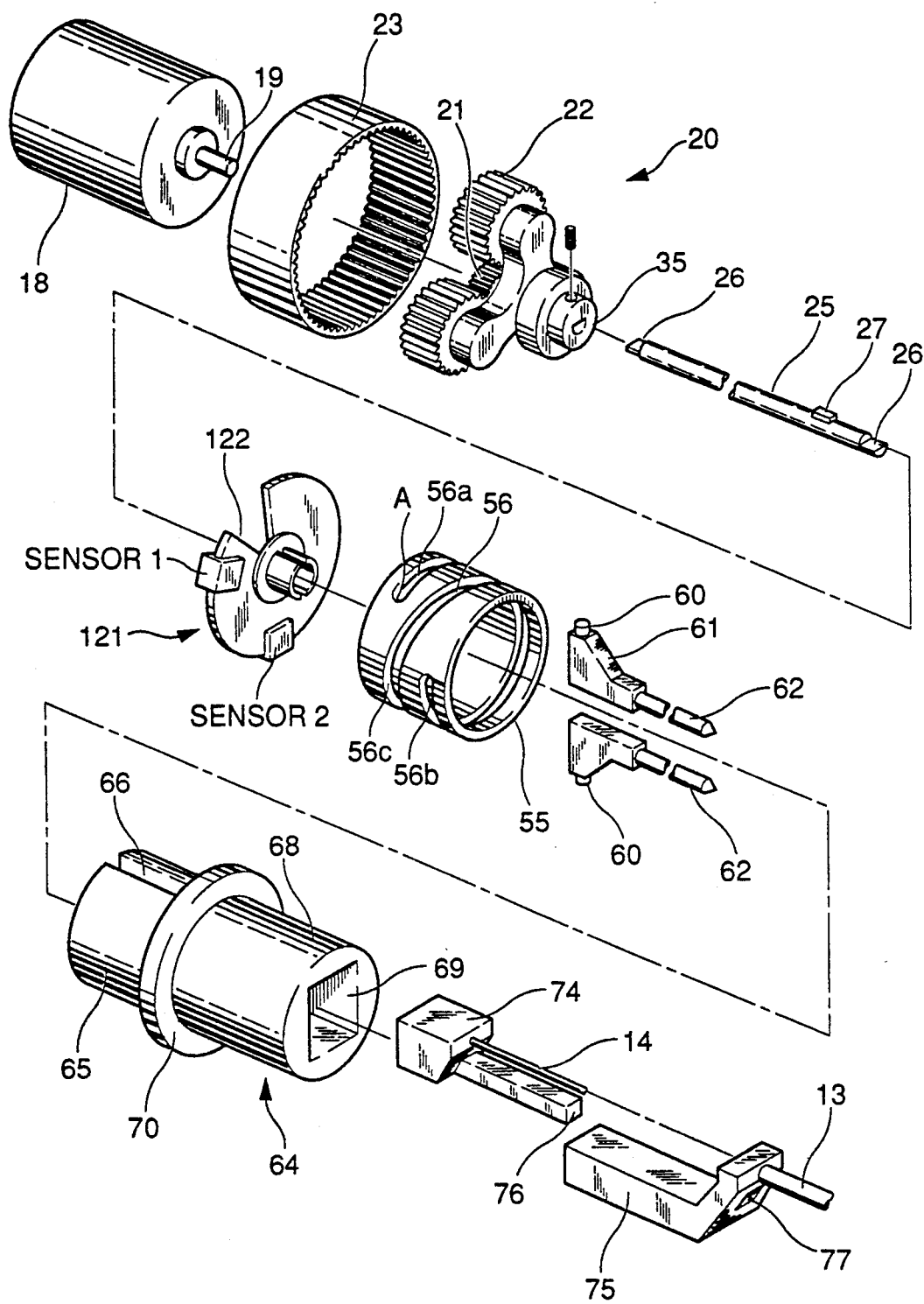
FIG. 4 is an exploded perspective view of the biopsy instrument further illustrating the major component parts thereof.
Figure 5:
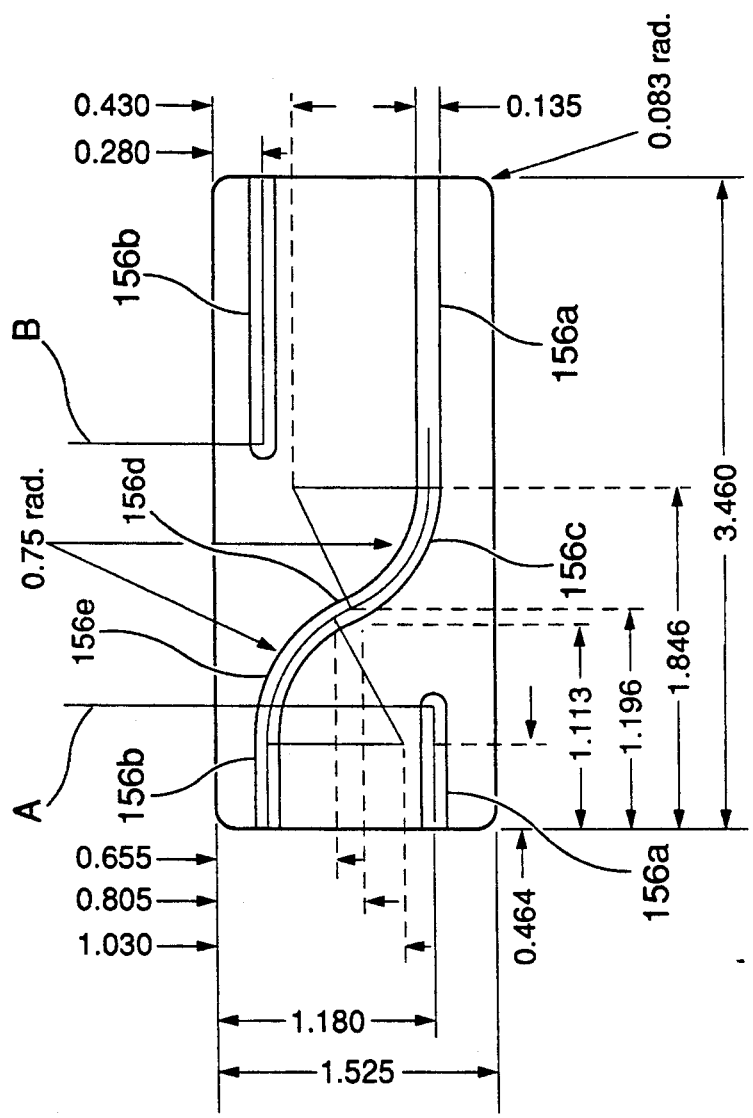
FIG. 5 is a plan view of the outer surface of the rotary cam illustrating the cam profile as a function of angular position about the full circumference of the cam.

The components of the instrument which guide the stylet/cannula assembly 12 will now be detailed. A physician or technician actuates the instrument causing the stylet 14 to move forward in a rapid and precise manner to penetrate the tissue mass followed by penetration of the mass by the cannula 13, resulting in a portion or core of tissue being severed and retained in the notched portion of the stylet. Further actuation causes the cannula to retract exposing the tissue sample in the notched portion at the distal end of the stylet for easy removal. An additional actuation causes retraction of the stylet and a resetting of the cannula/stylet assembly for further use. The penetration and retraction of the stylet and cannula assembly is controlled in part by hollow rotary cam 55, one embodiment of which is illustrated in FIG. 4. As will be described later, the cam preferably has a cam profile as illustrated in FIG. 5. Cam 55 is provided with a continuous groove 56 which is made up of three sections. A first groove section 56a is positioned substantially parallel to one end of cam 55 and extends about a portion of the circumference of the cam. A second groove section 56b is positioned substantially parallel to the other end of the cam and also extends about a portion of the circumference of the cam.

Section 56c connects section 56a and 56b in a generally diagonal manner in the embodiment of FIG. 4. Cam 55 is rotated by means of drive shaft 25, which is secured at its forward end 26 into the opening 63 of the end wall 59 of cam 55. Thus rotation of shaft 25 in a clockwise or counterclockwise direction causes identical rotation of the cam.

As previously described, stylet 14 moves within and is surrounded by cannula 13. The non-penetrating end of stylet 14 is mounted in stylet block 74. Correspondingly, the non-penetrating end of cannula 13 is mounted into cannula block 75. As shown in FIG. 4, stylet block 74 is provided with extension 76 which is in alignment with and moves through opening 77 of the cannula block 75 to aid in proper alignment of the stylet and cannula blocks and therefore the stylet/cannula assembly. An alternative construction of the stylet/cannula assembly is disclosed in U.S. Pat. No. 5,146,921, which is hereby incorporated by reference.

Mounted in the ends of each of the cannula and stylet blocks are drive rods 62 which are in turn secured to drive arms 61. Each of drive arms 61 is provided with a cam follower 60 which rides in the continuous groove 56 of cam 55. Thus, rotation of cam 55 will result in sequential linear movement of the stylet and cannula.

Although a generally diagonal central groove section 56c is useful with an optoelectronic sensor as shown in FIG. 4, the cam profile is preferably as illustrated in FIG. 5, which is a scale drawing of the outer surface of the cam, with the front edge of the cam appearing at the top of the drawing. The groove has a flat rear section 156a beginning at one end point A and extending approximately 235° counterclockwise (CCW) around the cam, as viewed from the rear, followed by a S-curve or sinusoidal section which includes sections 156c, 156d and 156e extending approximately 68°, 9° and 68° CCW, respectively, around the cam, followed by a flat front section 156b extending approximately 199° CCW around the cam, to the other end point B.

Fixed within the housing is a printed circuit board 120 on which is mounted all of the motor driver and control electronics for the instrument, as will be explained in detail in connection with FIG. 6. The board is provided with a central hole through which drive shaft 25 passes, as shown in FIG. 2. A slotted disc 121 is affixed to the drive shaft, preferably by means of a D-shaped opening mating with a D-shaped section on the shaft as in the case of the connection to the cam 55. The disc is positioned so as to pass through the openings in two optoisolators referred to herein as sensor 1 and sensor 2 and labeled #1 and #2, respectively, in FIG. 3. The slot in the disc is 50° wide, and the disc is fixedly mounted on the drive shaft such that edge 122 of the slot is angularly offset 9°-10° with respect to the endpoint A of the groove in the cam, as shown in FIG. 4. It will be appreciated by those skilled in the art that, although FIG. 4 shows cam followers 60 at the same axial position, this is for illustration purposes only in the exploded view, and that, in operation, the angular position of the cam in FIG. 4 corresponds to the stylet in a partially extended position.

Operation of the instrument begins with stylet 14 and cannula 13 in a retracted position and with the exposed tip of stylet 14 immediately adjacent the tissue mass 11. Initial rotation of cam 55 results in forward movement of stylet block 74 and its attached stylet to penetrate the tissue mass where a portion of the tissue is caught in notch 14a. Continued rotation of the cam results in forward movement of the cannula block 75 and its attached cannula into the tissue mass severing the portion of the tissue within notch 14a from the tissue mass. The instrument is then withdrawn from the patient. Rotation of cam 55 is then reversed thus causing retraction of the cannula exposing the tissue sample in notch 14a for easy removal by the technician. Further rotation of cam 55 will result in retraction of the stylet and, thus, a return to the initial ready-to-fire condition.

Because of the need for precise movement of stylet and cannula, guide means shown generally at 64 are used to further embodiment shown in FIG. 4, guide means 64 includes a generally cylindrical shaped housing 68 having a rectangular opening 69 approximately sized to accommodate the stylet and cannula blocks 74 and 75. Thus the stylet and cannula blocks move laterally within the interior of housing 68 and bear on the interior walls of the housing aiding proper alignment. In addition, guide means 64 also includes a cylindrical shaped guide 65 and bulkhead 70, the latter separating guide 64 and housing 68. Guide 65 is a solid cylinder provided with vertical channels 66 through which drive rods 62 operate. Guide 65 is constructed with a separator between channels 66 to assist in maintaining proper spacing and alighment of the drive rods.

In the preferred embodiment, the instrument has three actuators or buttons which set into motion the action of the stylet/cannula assembly. As shown in FIG. 1, the instrument includes retract button set 80 and a fire button 83, which are preferably provided with a rubber seal. The retract button set is located on the underside of the instrument and mechanically connected to two pairs of contacts 81 in a switch frame 89 which also includes a microswitch 85 mechanically connected to fire button 83. The retract button set includes separate buttons for the cannula and stylet, preferably positioned side by side. Thus, the instrument has three separate pushbutton switches: (1) a fire switch, (2) a cannula retract switch, and (3) a stylet retract switch. Actuation of the fire button, when enabled, causes initial penetration of the stylet into the tissue mass followed by penetration of the cannula. Actuation of the cannula retract button, when enabled, causes retraction of the cannula exposing the sample of tissue. Actuation of the stylet retract button, when enabled, retracts the stylet whereupon the instrument is ready for further use.

Figure 6:
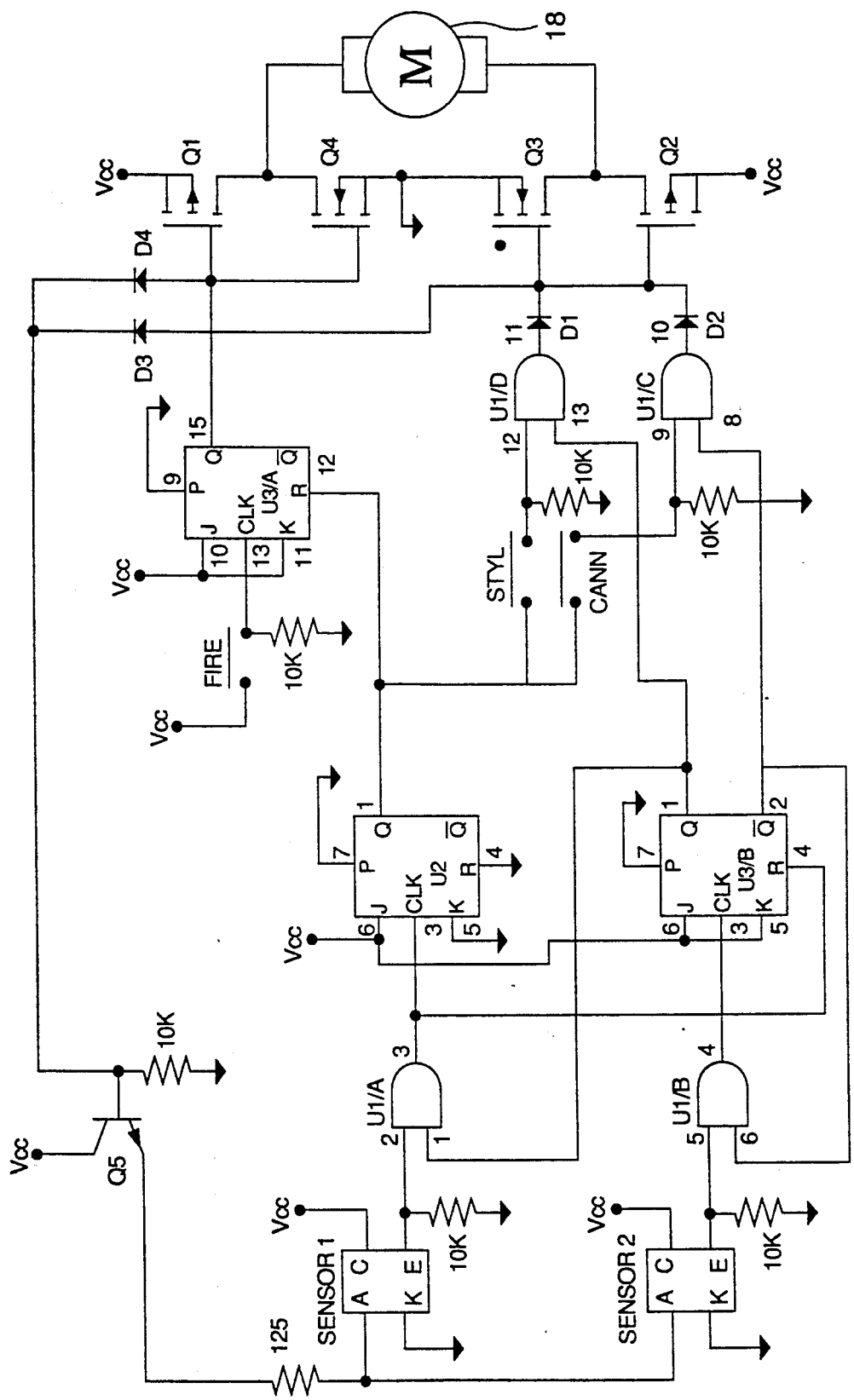
FIG. 6 is an electrical schematic of a control circuit according to the preferred embodiment of this invention.

Referring now to FIG. 6, which is an electrical schematic for the preferred embodiment of the motor driver and control electronics according to this invention, the primary components of the circuitry are three JK flip-flops, four AND gates, two complementary pairs of MOSFETs, and two optoisolators which return mechanical position data. U2 and U3/B operate in conjunction with each other to dictate which operator button is enabled via U3/A, U1/C and U1/D. Another function of U3/B is to dictate which sensor output is enabled via U1/A and U1/B. U3/A is primarily a latching circuit for the fire button.

In the ready-to-fire position, which is the proper initial position for operation of the device, the stylet and cannula are both retracted and the circuit is in a reset or standby mode. In this mode the outputs (Q1) of all three JK flip-flops are low (logic "0"), thus disabling sensor 1, enabling sensor 2 and enabling the fire button and fire latch U3/A.

Once the fire button is pressed, the output of U3/A goes high (logic "1"), turning on the LEDs in sensors 1 and 2 through transistor Q5 and forward biasing MOSFET Q4, thereby connecting one terminal of the drive motor to ground. U1/C and U1/D are both held low at this time by the low levels on the Q outputs of JK flip-flops U2 and U3/A. Thus, MOSFET Q2 is on, enabling motor drive current to flow from VCC through Q2, the motor, and Q4 to ground.

Therefore, in response to actuation of the fire button, the drive motor begins turning and, through the planetary gear box, causes the drive shaft to rotate clockwise (CW) as viewed from the rear of the instrument. This causes the slotted disc to rotate clockwise from its initial position, in which the slot is adjacent to sensor 1 which is located directly below the drive shaft. Sensor 2, located 120° counterclockwise from sensor 1 as viewed from the rear of the instrument, detects the passage of the slot after approximately 230° of clockwise shaft rotation, and, in response, generates an output pulse which passes through U1/B, enabled at this time by a high state output on the $\overline{Q}$ output of U3/B, and clocks U3/B, thereby disabling sensor 2 and enabling sensor 1. The motor continues to drive the rotary cam and slotted disc clockwise until the slot returns to a point adjacent sensor 1, which responds by clocking U2 through U1/A. U2 goes high in response, resetting U3/A and thereby stopping the motor. The low output from U3/A not only turns off Q4 and thereby deenergizes the motor, but also turns on Q1 to connect both terminals of the motor to VCC, thereby providing dynamic braking. The motor stops with the stylet and cannula in their extended positions.

The high output from U2 is also supplied to one contact of each of the stylet and cannula retract switches as an enabling signal. With U3/B reset at this time, only the cannula retract switch is actually enabled, because the low Q output of U3/B prevents any pulse from the stylet retract switch from passing through U1/D. When the cannula retract button is pressed, the output of U1/C goes high, turning on transistor Q3 and completing a circuit from VCC through Q1, the motor and Q3 to ground, whereby the motor reverses direction and causes the rotary cam and slotted disc to rotate counterclockwise. It should be noted, perhaps, that both optoelectronic sensors are disabled whenever the motor is deenergized. Once cannula retraction begins, however, both sensor LEDs are again turned on through Q5, although only sensor 2 is enabled because U1/A is disabled at this time. Thus, sensor 2 is the first sensor to respond to the passage of the slot in the slotted disc, and it responds by clocking U3/B, thereby disabling sensor 2 and the cannula retract button and enabling sensor 1 and the stylet retract button. The motor stops in response to the resulting low state at the output of U1/C.

The final step in the cycle is actuation of the stylet retract button. Pressing this button with U1/D enabled re-enables the drive, causing the cam and slotted disc to resume counterclockwise rotation and resulting in sensor 1 clocking U2 and resetting U3/B through U1/A. This disables the stylet retract button and re-enables the fire latch, thereby completing the full cycle.

The instrument's response time is short enough that movement from any one of the predefined extended or retracted positions is completed before any of the control buttons can be released in normal operation.

The presently preferred components are specified as follows:

| Device | Device Type |
| --- | --- |
| U1 | CD 4081B |
| U2, U3 | CD 4027B |
| Q1, Q2 | ECG 2382 |
| Q3, Q4 | ECG 2383 |
| Sensors 1, 2 | EE-SX 1067 |

The invention is described above in terms of optoisolators and a slotted disc as the preferred position sensor construction, primarily because of superior speed of response. However, the present invention, more broadly, contemplates the elimination of spring fingers or other wiper elements and wiper plates of the type disclosed in U.S. Pat. No. 4,940,061. The term "wiperless position sensor" is used in this patent to mean any type of limit switch or other position sensor which does not have such a wiper assembly, and is intended to include optoelectronic devices, electromagnetic devices, Hall effect devices, capacitive devices, and microswitches, among others.

The present invention has a number of advantages over all other forms of biopsy instruments including that disclosed in U.S. Pat. No. 4,940,061. In addition to greater reliability as a result of a wiperless position sensor, the instrument has improved action because of the new cam profile, as shown in FIG. 5. The curved section of the cam extends less than 145° around the cam circumference, without abrupt transitions, and begins approximately 55° from the fully retracted position of the cam follower for the stylet. One advantage of this construction is a large increase in the amount of time the motor spends in a no-load condition upon starting, thus allowing the motor to accelerate and reach a motor speed above the loaded rating prior to hitting the ramp in the cam. This increase in speed directly results in desired higher needle velocities. The reduction in ramp length results in greater forward movement per degree of rotation, further increasing the maximum needle velocity during the stroke. Another desirable feature is a small delay between the time the stylet finishes its stroke and the time the cannula begins its stroke. This allows more tissue to fall into the slotted stylet, and thereby results in improved core samples.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An electronic biopsy instrument, comprising:
   a cannula;
   a stylet slidably mounted in said cannula;
   electromechanical actuator means for producing sequential linear motion of said stylet and cannula, said actuator means including means for extending said stylet and thereafter extending said cannula, and means for producing reciprocating motion of said stylet and cannula;
   position sensing means for sensing the position of said cannula;
   electronic control means connected to said position sensing means for controlling said actuator means, said control means including means responsive to said position sensing means for stopping the motion of said stylet and cannula when said cannula reaches a predefined extended position whereby said cannula and stylet are both extended, when said cannula reaches a predefined retracted position whereby said cannula is retracted and said stylet is extended, and when said stylet reaches a predefined retracted position whereby said cannula and said stylet are both retracted; and switch means for actuating said electronic control means;

wherein said position sensing means includes first means for detecting when said cannula reaches said predefined extended position and when said stylet reaches said predefined retracted position, and second means for detecting when said cannula reaches said predefined retracted position, said first and second means for detecting comprising first and second wiperless sensors, respectively.

2. The electronic biopsy instrument of claim 1, wherein said position sensing means includes an optoelectronic sensor.

3. An electronic biopsy instrument, comprising:
a cannula;
a stylet slidably mounted in said cannula;
electromechanical actuator means for producing sequential linear motion of said stylet and cannula, said actuator means including means for extending said stylet and thereafter extending said cannula, and means for producing reciprocating motion of said stylet and cannula;
position sensing means including an optoelectronic sensor for sensing the position of said cannula;
electronic control means connected to said position sensing means for controlling said actuator means, said control means including means responsive to said position sensing means for stopping the motion of said stylet and cannula when said cannula reaches a predefined extended position whereby said cannula and stylet are both extended, when said cannula reaches a predefined retracted position whereby said cannula is retracted and said stylet is extended, and when said stylet reaches a predefined retracted position whereby said cannula and said stylet are both retracted; and
switch means for actuating said electronic control means;
wherein said position sensing means includes first means for detecting when said cannula reaches said predefined extended position and when said stylet reaches said predefined retracted position, and second means for detecting when said cannula reaches said predefined retracted position, said first and second means for detecting comprising first and second optoelectronic sensors, respectively.

4. The electronic biopsy instrument of claim 3, wherein said actuator means includes an electric motor, a drive shaft, and a rotary cam coupled to said drive shaft for translating rotary motion to linear motion,
and wherein said position sensing means is responsive to the angular position of said rotary cam, said first and second means for detecting including stationary first and second optoisolators, respectively, and a common slotted disc rotatably coupled to said drive shaft.

5. The electronic biopsy instrument of claim 4, wherein said cam has an S-curve profile.

6. An electronic biopsy instrument, comprising:
a cannula;
a stylet slidably mounted in said cannula;
electromechanical actuator means for producing sequential linear motion of said stylet and cannula, said actuator means including means for extending said stylet and thereafter extending said cannula;
position sensing means for sensing the position of said cannula;
electronic control means connected to said position sensing means for controlling said actuator means; and
switch means for actuating said electronic control means;
wherein said actuator means includes an electric motor, a drive shaft, and a rotary cam coupled to said drive shaft for translating rotary motion to linear motion,
and wherein said position sensing means includes first and second means for sensing the angular position of said rotary cam, said first and second means including first and second optoelectronic sensors, respectively, first and second, respectively, and a common slotted disc rotatably coupled to said drive shaft.

7. The electronic biopsy instrument of claim 6, wherein said cam has an S-curve profile.

8. An electronic biopsy instrument, comprising:
a cannula;
a stylet slidably mounted in said cannula;
electromechanical actuator means for producing sequential linear motion of said stylet and cannula, said actuator means including means for extending said stylet and thereafter extending said cannula, and means for producing reciprocating motion of said stylet and cannula;
position, sensing means for sensing the position of said cannula;
electronic control means connected to said position sensing means for controlling said actuator means, said control means including means responsive to said position sensing means for stopping the motion of said stylet and cannula when said cannula reaches a predefined extended position whereby said cannula and stylet are both extended, when said cannula reaches a predefined retracted position, whereby said cannula is retracted and said stylet is extended, and when said stylet reaches a predefined retracted position whereby said cannula and said stylet are both retracted; and
switch means for actuating said electronic control means,
wherein said electronic control means includes means for limiting extension of said stylet and cannula by said actuator means to a single forward motion and single rearward motion per actuation of said switch means;
and wherein said position sensing means includes first sensor means for detecting when said cannula reaches said predefined extended position and when said stylet reaches said predefined retracted position, and second means for detecting when said cannula reaches said predefined retracted position, said first and second means for detecting comprising first and second wiperless sensors, respectively.

9. The electronic biopsy instrument of claim 8, wherein said position sensing means includes an optoelectronic sensor.

10. An electronic biopsy instrument, comprising:

a cannula;

a stylet slidably mounted in said cannula;

electromechanical actuator means for producing sequential linear motion of said stylet and cannula, said actuator means including means for extending said stylet and thereafter extending said cannula;

position sensing means including an optoelectronic sensor for sensing the position of said cannula;

electronic control means connected to said position sensing means for controlling said actuator means, said control means including means responsive to said position sensing means for stopping the motion of said stylet and cannula when said cannula reaches a predefined extended position whereby said cannula and stylet are both extended, when said cannula reaches a predefined retracted position whereby said cannula is retracted and said stylet is extended, and when said stylet reaches a predefined retracted position whereby said cannula and said stylet are both retracted; and switch means for actuating said electronic control means, wherein said electronic control means includes means for limiting extension of said stylet and cannula by said actuator means to a single forward motion and single rearward motion per actuation of said switch means;

and wherein said position sensing means includes first means for detecting when said cannula reaches said predefined extended position and when said stylet reaches said predefined retracted position, and second means for detecting when said cannula reaches said predefined retracted position, said first and second means for detecting comprising forst and second optoelectronic sensors, respectively.

11. The electronic biopsy instrument of claim 10, wherein said actuator means includes an electric motor, a drive shaft, and a rotary cam coupled to said drive shaft for translating rotary motion to linear motion, and wherein said position sensing is responsive to the angular position of said rotary cam, said first and second means for detecting including stationary first and second optoisolators, respectively, and a common slotted disc coupled to said drive shaft.

12. The electronic biopsy instrument of claim 11, wherein said cam has an S-curve profile.

13. An electronic biopsy instrument, comprising:

a cannula;

a stylet slidably mounted in said cannula;

electromechanical actuator means for producing sequential linear motion of said stylet and cannula, said actuator means including means for extending said stylet and thereafter extending said cannula;

position sensing means for sensing the position of said cannula;

electronic control means connected to said position sensing means for controlling said actuator means; and switch means for actuating said electronic control means, wherein said electronic control means includes means for limiting extension of said stylet and cannula by said actuator means to a single forward motion and single rearward motion per actuation of said switch means;

wherein said actuator means includes an electric motor, a drive shaft, and a rotary cam coupled to said drive shaft for translating rotary motion to linear motion, and wherein said position sensing means includes first and second means for sensing the angular position of said rotary cam said first and second means including first and second optoelectronic sensors, respectively, first and second, respectively, and a common slotted disc coupled to said drive shaft.

14. The electronic biopsy instrument of claim 13, wherein said cam has an S-curve profile.

* * * * *

UNITED STATES PATENT AND TRADEMARK OFFICE
CERTIFICATE OF CORRECTION

PATENT NO. : 5,249,583

DATED : October 5, 1993

INVENTOR(S) : Mark Mallaby

It is certified that error appears in the above-identified patent and that said Letters Patent is hereby corrected as shown below:

Drawings:

In FIG. 4, please change "SENSOR 1" to --SENSOR 2-- and vice versa.

In column 5, line 34, please delete "a".

In column 6, line 12, after "further" please insert: --aid in proper alignment of the stylet/cannula assembly. In the--.

In column 6, line 25, please change "alighment" to --alignment--.

In column 10, line 22, please delete "first and second, respectively,".

In column 10, line 36, please delete the comma after "position".

In column 10, line 46, please delete the comma after "position".

In column 10, line 58, please delete "sensor".

In column 11, line 34, please change "forst" to --first--.

In column 12, line 1, please insert --means-- after "sensing".

In column 12, line 33, please insert a comma after "cam".

In column 12, line 35, please delete "first and second, respectively,".

UNITED STATES PATENT AND TRADEMARK OFFICE
CERTIFICATE OF CORRECTION

PATENT NO. : 5,249,583
DATED : October 5, 1993
INVENTOR(S) : Mark Mallaby

It is certified that error appears in the above-identified patent and that said Letters Patent is hereby corrected as shown below:

In column 6, line 12, after "further" please insert: --aid in proper alignment of the stylet/cannula assembly. In the--.
    In column 6, line 25, please change "alighment" to --alignment--.
    In column 10, line 22, please delete "first and second, respectively,".
    In column 10, line 36, please delete the comma after "position".
    In column 10, line 46, please delete the comma after "position".
    In column 10, line 58, please delete "sensor".
    In column 11, line 34, please change "forst" to --first--.
    In column 12, line 1, please insert --means-- after "sensing".
    In column 12, line 33, please insert a comma after "cam".
    In column 12, line 35, please delete "first and second, respectively,".

Signed and Sealed this

First Day of February, 1994

Attest:

BRUCE LEHMAN

*Attesting Officer*    *Commissioner of Patents and Trademarks*